United States Patent
Hayashi et al.

(10) Patent No.: US 6,410,557 B2
(45) Date of Patent: Jun. 25, 2002

(54) DRY SKIN REMEDIES

(75) Inventors: Keiji Hayashi, Matsudo; Hirohiko Arisawa, Minamikawachi-machi; Hiroaki Masunaga, Mibu-machi, all of (JP)

(73) Assignee: Daiichi Pharmaceutical Col, Ltd., Tokyo (JP)

( * ) Notice: Subject to any disclaimer, the term of this patent is extended or adjusted under 35 U.S.C. 154(b) by 0 days.

(21) Appl. No.: 09/898,256

(22) Filed: Jul. 5, 2001

Related U.S. Application Data

(63) Continuation of application No. PCT/JP00/00120, filed on Jan. 13, 2000.

Foreign Application Priority Data

Jan. 14, 1999 (JP) ............................................. 11-008238

(51) Int. Cl.$^7$ ........................ A61K 31/44; C07D 453/00
(52) U.S. Cl. ..................... 514/305; 514/305; 514/278; 514/306; 546/18; 546/19
(58) Field of Search ................ 514/305, 278; 546/18, 19

(56) References Cited

U.S. PATENT DOCUMENTS

| | | | | |
|---|---|---|---|---|
| 4,855,290 A | * | 8/1989 | Fisher et al. | 515/278 |
| 4,861,886 A | * | 8/1989 | Haga et al. | 546/16 |
| 4,876,260 A | * | 10/1989 | Fisher et al. | 514/278 |
| 5,340,821 A | * | 8/1994 | Abe et al. | 514/305 |
| 5,571,918 A | * | 11/1996 | Hayashi et al. | 546/18 |
| 5,580,880 A | * | 12/1996 | Handa et al. | 514/305 |
| 6,235,291 B1 | * | 5/2001 | De La Charriere et al. | 424/401 |
| 6,331,307 B1 | * | 12/2001 | Sebillotte-Arnaud et al. | 424/401 |

FOREIGN PATENT DOCUMENTS

| | | | |
|---|---|---|---|
| JP | 01-290680 | 11/1989 | |
| JP | 08-092089 | 4/1996 | A61K/31/435 |

* cited by examiner

*Primary Examiner*—Sabiha Qazi
(74) *Attorney, Agent, or Firm*—Palmer & Dodge LLP

(57) ABSTRACT

Novel dry skin remedies useful for treatment dry skin, containing as the active ingredient spiro [oxathiolane-quinuclidine] derivatives represented by general formula (I) or acid addition salts thereof, desirably cis-2-methylspiro [1,3-oxathiolane-5,3'-quinuclidine] hydrochloride. The remedies promote the secretion of sebaceous and sweat glands through oral or parenteral administration to treat dry skin, thus being useful as drugs.

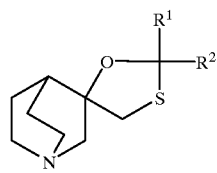

(I)

3 Claims, 1 Drawing Sheet

DRY SKIN REMEDIES

This application claims priority to International Application No. PCT/JP00/00120, filed Jan. 13, 2000, which in turn claims priority to Japanese Application No. 008238/1999, filed Jan. 14, 1999.

TECHNICAL FIELD

The present invention relates to a novel dry skin remedies.

Description Background Art

The term "dry skin" refers to abnormal dryness of the skin over the entire body of a patient, and is used as a generic term for various symptoms caused by such a condition. The skin has various sebaceous glands and perspiratory glands and proper moisture is maintained by secretion of sebum and sweat therefrom. The abnormal skin dryness is caused by xeroderma, atopic dermatitis, and other various skin diseases; immunologic diseases such as skin allergy or Sjogren's syndrome; metabolic diseases such as diabetes and liver disease; hormones imbalance such as postmenopausal hormones imbalance; various xerosises; administration of drugs or radiation exposure; or being placed in a dry region or dry environment; and the like. Besides the dry skin caused by such nosogenesis, there is also cryptogenic dry skin. Patients having dry skin feel dryness of the skin all over the body or topical dryness of the skin. Actual symptoms include flaring of the skin, itching (pruruitus), pain, crevice, chapped skin, or bleeding by scratching, or sclerema by chronic dry skin. These symptoms constitute severe problems in daily life.

Generally a moisturizing agent such as toilet water, creams, and lotions is used to alleviate the dryness symptoms. However, since this has a temporary effect, it must be applied often, and in some cases causes skin allergy. For curing the hormone imbalance, various hormone preparations are administered, but they have specific adverse effects. A steroid ointment can be used therapeutically as well. However, it may cause skin atrophy or fungus induction, therefore, it can only be used under limited conditions. Because of this, the treatment technique thereof has not yet been established.

Disclosure of the Invention

In view of the above-described situation, the present inventors have extensively studied substances which promote the secretion of sweat to control the dryness of the skin and has few side effects as well as little toxicity. As a result, the inventors have found that a derivative of spirooxathiolane quinuclidine or an acid addition salt thereof, which has been known as a therapeutic agent for the treatment of diseases of the central nervous system, promotes the secretion of sweat from the perspiratory gland in the skin over the entire body. Therefore, an object of the present invention is to provide a novel therapeutic agent for the treatment of dry skin. More specifically an object of the present invention is to provide a novel therapeutic agent for the treatment of dry skin which contains a derivative of spirooxathiolane quinuclidine or an acid addition salt thereof as the active ingredient.

The present invention provides a therapeutic agent for the treatment of dry skin, containing a derivative of spirooxathiolane quinuclidine or an acid addition salt thereof, represented by the following formula (I), as an active ingredient:

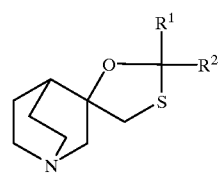

(I)

wherein, $R_1$ and $R^2$ may be the same or different, and each represents hydrogen, or an alkyl, cyclopentyl, cyclohexyl, aryl, diarylmethylol group or an alkyl group which is substituted by one or more aryl groups.

The term alkyl used herein refers to lower alkyl groups having 1-6 carbon atoms, such as methyl, ethyl, propyl, isopropyl, butyl, s-butyl, t-butyl, amyl and hexyl. The term aryl used herein refers to phenyl, tolyl, xylyl, diphenyl, diphenylmethyl, and the like.

A preferable spirooxathiolane quinuclidine derivative or an acid addition salt thereof, which is the active ingredient used in the present invention, is preferably 2-methylspiro (1,3-oxathiolane-5,3')quinuclidine hydrochloride, in particular the cis-isomer.

BEST MODE FOR CARRYING OUT THE INVENTION

Figure 1:
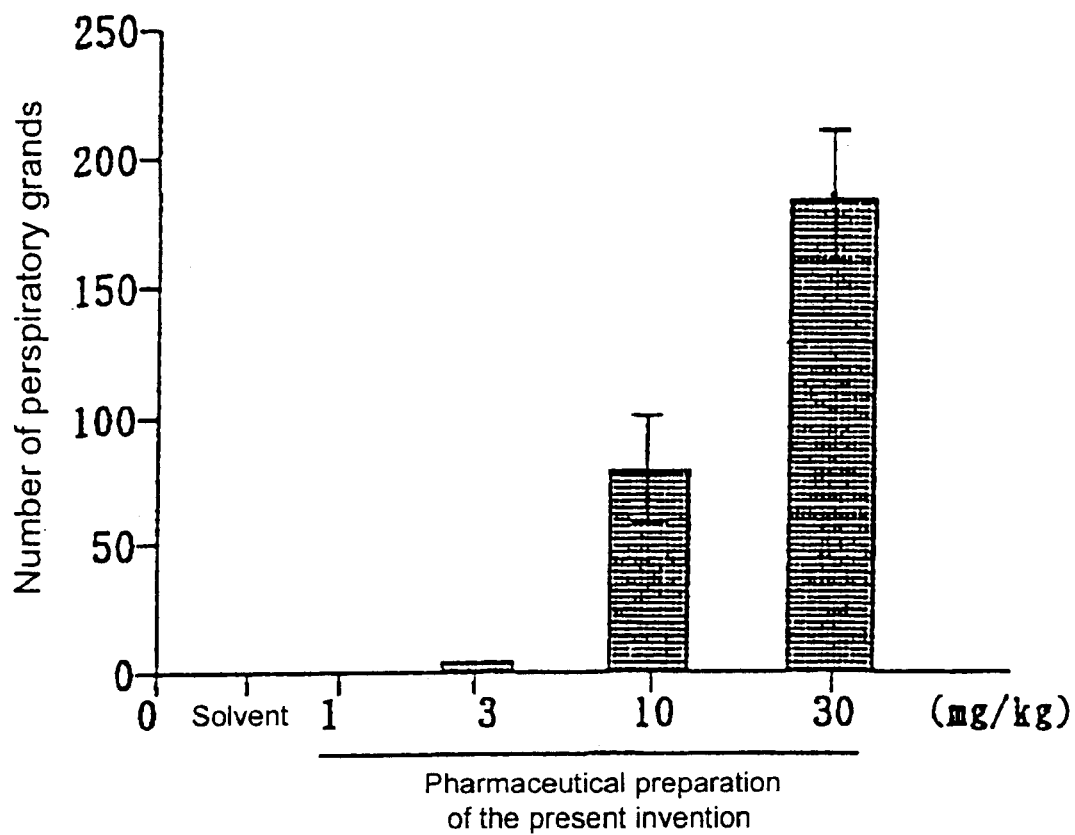
FIG. 1 is a graph showing the degree of perspiration caused by the pharmaceutical preparation of example 1 according to the present invention.

The present invention relates to a therapeutic agent for the treatment of dry skin, which contains a derivative of spirooxathiolane quinuclidine represented by the above-mentioned formula (I) and an acid addition salt thereof as the active ingredient.

The derivative of spirooxathiolane quinuclidine and an acid addition salt thereof employed according to the present invention are known compounds disclosed in Japanese Patent Laid-Open No.280497/1986. The derivatives of spirooxathiolane quinuclidine used in the present invention are as follows.

(1) 2-Methylspiro (1,3-oxathiolane-5,3') quinuclidine
(2) 2-Diphenylmethylspiro (1,3-oxathiolane-5,3') quinuclidine
(3) 2-Methyl-2-phenylspiro(1,3-oxathiolane-5,3') quinuclidine These compounds can be in the form of geometrical isomers, enantiomers, diastereomers or racemates. According to the present invention, any of theses forms may be used. The acid addition salts thereof include acid addition salts with both inorganic and organic acids such as hydrochloric acid, sulfuric acid, phosphoric acid, sulfamic acid, lactic acid, tartaric acid, succinic acid, and maleic acid. Among these compounds, 2-Methylspiro(1,3-oxathiolane-5, 3')quinuclidine hydrochloride is preferably employed, and in particular its cis-isomer or a mixture of a cis-isomer and a trans-isomer in which the cis-isomer is dominantly contained are preferably employed.

The derivative of spirooxathiolane quinuclidine according to the present invention can be prepared by the method disclosed in the publication of Japanese Patent Laid-Open No. 280497/1986. For example, it can be easily obtained by reacting 3-hydroxy-3-mercaptomethyl-quinuclidine with a carbonyl compound represented by the formula $R^1$—CO—$R^2$ (wherein $R^1$ and $R^2$ are the same group as above) as shown by formula (II), followed by isolation of the objective compound from the reaction mixture. The equation can be shown as follows. Isolation of an optical isomer or other isomers from the obtained compounds can be carried out, for example, by the methods described in Japanese Patent Laid-Open No. 280497/1986 or Japanese Patent Laid-Open No. 22280/1990.

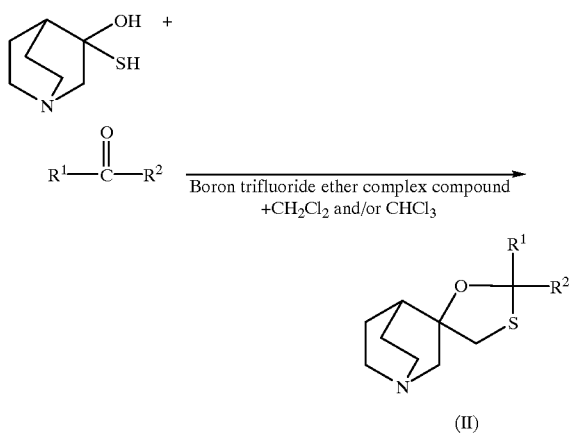

The dry skin therapeutic agent according to the present invention can be orally or parenterally administered as an excellent drug to human and animals. When the therapeutic agent for the treatment of dry skin according to the present invention is applied to cure the disease, the compound according to the present invention is administered as an active ingredient singly, or combined with pharmaceutically acceptable carriers in a suitable dosage form of pharmaceutical composition for oral, parenteral, topical or rectal administration such as capsules, tablets, packaged powders, granules, injections, ointments, suppositories.

As examples of pharmaceutical preparations suitable for oral administration, solid compositions such as capsules, tablets, powders, granules, or troches and liquid compositions such as syrups or suspensions can be given. According to the present invention, these compositions for oral administration such as capsules, tablets and granules are prepared by conventional methods, using as vehicles, for example, starch, lactose, white sugar, mannitol, carboxymethylcellulose, corn starch, and inorganic salts, etc. Other than the above-described vehicles, binders, disintegrators, surfactants, lubricants, fluidity accelerators flavors, colorants, perfumes etc., can also be used.

More specifically, as examples of a binder, starch, dextrin, powdered acacia, gelatin, hydroxypropyl starch, methylcellulose, sodium carboxymethyl cellulose, hydroxypropyl cellulose, crystalline cellulose, ethyl cellulose, polyvinyl pyrolidone and Macrogol™ can be given. As examples of a disintegrator, starch, hydroxypropyl starch, sodium carboxymethyl cellulose, cross-linked sodium carboxymethyl cellulose, calcium carboxymethyl cellulose, carboxymethyl cellulose and low-substituted hydroxypropyl cellulose and the like can be given.

As examples of a surfactant, sodium lauryl sulfate, soybean lecithin, sucrose fatty acid esters, Polysolvate 80™ and the like can be given. As examples of a lubricant, talc, waxes, hydrogenated vegetable oils, sucrose fatty acid esters, magnesium stearate, calcium stearate, aluminum stearate, polyethylene glycol and the like can be given. As examples of a fluidity accelerator, light silicic acid anhydride, dry aluminum hydroxide gel, synthetic aluminum silicate, magnesium silicate and the like can be given.

For oral administration, the compound can be administered in a dosage form such as a suspension, emulsion, syrup, and elixir, which may contain a flavor and a colorant etc.

It is desirable that these compositions contain 1-95% by weight of an active ingredient.

As examples of pharmaceutical preparations suitable for parenteral administration, injections can be given. These parenteral formulations are prepared according to conventional methods and, generally, distilled water for injection, physiological saline, an aqueous glucose solution, vegetable oils for injection, sesame oil, peanut oil, soybean oil, corn oil, propylene glycol, polyethylene glycol, etc., can be used as a diluent. In addition, an antibacterial agent, a preservative, and a stabilizer may be added, if necessary. Considering the stability of compositions of parenteral administration, they can be filled in vials or the like, frozen and lyophilized by conventional methods so that the water therein is removed, followed by reconstitution of solutions from lyophilized compositions just before their use. In addition, if necessary, isotonic agents, stabilizers, preservatives, soothing agents, etc., may be added appropriately.

An injection preparation may by prepared by dissolving the compound of the present invention, for example, in a salt form, in water for injection or may be prepared in a dosage form suitable for injection, such as a suspension or an emulsion of admixture of the compound of the present invention with a pharmaceutically acceptable oil or liquid. In these cases, antibacterial agents such as benzyl alcohol, antioxidants such as ascorbic acid, buffers, osmoregulating agents, solubilizer, may be added.

It is preferable for the injection-preparation to contain 0.1-5% by weight of an active ingredient. This can be used in a dosage form for intravenous, intraarterial, intramuscular or subcutaneous injection.

As examples of a pharmaceutical preparation suitable for topical or rectal administration, ointments, suppositories and the like can be given. Ointments can be prepared by adding the compound of the present invention to basic vehicles according to a conventional method. It is preferred that the ointments contain 0.5–30% by weight of an active ingredient. Suppositories may comprise pharmaceutical carriers known in the art, such as polyethylene glycol, lanolin, cacao fat, fatty acid triglycerides.

It is preferred that the suppositories contain 1–95% by weight of an active ingredient.

The above pharmaceutical preparations can be prepared, according to the method known in the art, in order to release an active component rapidly, slowly or retardedly after administration to a patient.

The dose level of the therapeutic agent of the present invention for the treatment of dry skin shall be decided depending on, and varying with, the dosage form, administration method, purpose of application, and the age, body weight, and disease conditions of a patient. Generally, the amount of the active ingredient contained in the preparation is appropriately in a range of from about 1 mg to about 1 g per one adult. The content of an active ingredient in a pharmaceutical preparation is appropriately determined according to the above dose level. The agent may be administered once or in several portions a day.

EXAMPLES

The present invention is further described more in detail in the following examples, but these are only for illustration of the embodiments of the present invention and not for restricting the present invention.

Example 1

A Promoting Action on the Secretion of Sweat in Rat Foot Skin

A pharmacological activity test was carried out using 6 male Wister rats (body weight 199–238 g) in one group. After fasting for 1 day, rats were anesthetized by 50 mg/kg of sodium pentobarbital which was intraperitoneally administered, and an endotracheal tube was inserted to maintain the airway.

The soles of the right and left feet were cleaned with 70% ethanol, then 95% ethanol containing 2% of iodine was applied and allowed to dry. Castor oil containing 50% corn starch was coated to the soles of both feet, 5 minutes later a solvent alone or 1,3,10, and 30 mg/kg of cis-2-methylspiro (1,3-oxathiolane-5,3')quinuclidine hydrochloride were administered intravenously. As the sweating part of the soles of feet showed coloration due to the starch-iodine reaction, the number of colored points on the soles of both feet (number of perspiratory glands) were counted and the degree of perspiration was measured. The results are given in FIG. 1.

The results show that the sweat secretion on the soles of both feet was promoted depending on the dose level of the quinuclidine hydrochloride. Also it was confirmed that atropine blocks this activity. Accordingly, it was found that the pharmaceutical preparation according to the present invention is effective in preventing and/or curing dry skin.

Example 2

Perspiration Promoting Action in the Clinical Test on Humans

A multi-facility double blind comparison study was carried out for examination of perspiration promoting action on human, by preparing capsules containing 30 or 60 mg of cis-2-methylspiro(1,3-oxathiolane-5,3')quinuclidine hydrochloride. 75 Americans (69 White, 1 Black, and 5 Hispanic subjects) were divided into 3 groups randomly. Each group received either one placebo capsule (0 mg), one 30 mg capsule, or one 60 mg capsule orally administered three times a day for 6 weeks. The increase of perspiration in each group was tested. The results are given in Table 1.

TABLE 1

| Subject Group | Number of Subjects | Number of Subjects Showing perspiration (%) |
|---|---|---|
| Placebo administered group (0 mg × 3/day) | 23 | 1 (4.3%) |
| 30 mg capsule administered (30 mg × 3/day) | 25 | 4 (16.0%) |
| 60 mg capsule administered group (60 mg × 3/day) | 27 | 13 (48.1%) |

The results confirmed that sweat secretion of human was remarkably promoted by administration of capsules containing cis-2-methylspiro(1,3-oxathiolane-5,3')quinuclidine hydrochloride.

Example 3

Production of Pharmaceutical Preparation

Preparation Example 1: Capsules

Capsules of the following composition were prepared according to a conventional method.

| | |
|---|---|
| cis-2-Methylspiro(1,3-oxathiolane-5,3')quinuclidine hydrochloride | 10 g |
| Low-substituted hydroxypropylcellulose (L-HPC) | 20 g |
| Cross-linked carboxymethylcellulose sodium salt (Cross-linked CMC-Na) | 5 g |
| Magnesium stearate | 2 g |
| Lactose | proper quantity |
| | 100 g |

Preparation Example 2: Tablets

Tablets of the following composition were prepared according to a conventional method.

| | |
|---|---|
| cis-2-Methylspiro(1,3-oxathiolane-5,3')quinuclidine hydrochloride | 20 g |
| Low-substituted hydroxypropylcellulose (L-HPC) | 10 g |
| Crystalline cellulose | 15 g |
| Hydroxypropylmethylcellulose (HPMC) | 10 g |
| Magnesium stearate | 1 g |
| Lactose | proper quantity |
| | 100 g |

Preparation Example 3: Injection Solutions

Injection solutions of the following composition were prepared according to a conventional method.

| | |
|---|---|
| cis-2-Methylspiro(1,3-oxathiolane-5,3')quinuclidine Hydrochloride | 1 g |
| Glucose | 10 g |
| Distilled water for injection | proper quantity |
| | 200 ml |

Industrial Applicability

According to the present invention, a therapeutic agent for the treatment of dry skin is provided containing a derivative of spirooxathiolane quinuclidine and an acid addition salt thereof as an active ingredient. The pharmaceutical preparations according to the present invention have an excellent effect on dry skin and are useful as drugs.

What is claimed is:

1. A therapeutic agent for the treatment of dry skin, comprising a compound represented by the following formula (I) or an acid addition salt thereof as an active ingredient;

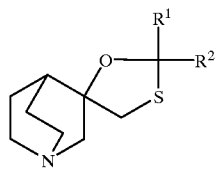

(I)

wherein, $R^1$ and $R^2$ may be the same or different, and each represents hydrogen, alkyl, cyclopentyl, cyclohexyl, aryl, or diarylmethilol groups or an alkyl group which is substituted by one or more aryl groups.

2. A therapeutic agent for the treatment of dry skin according to claim 1, wherein the acid addition salt is 2-methylspiro (1,3-oxathiolane-5,3')quinuclidine hydrochloride.

3. A therapeutic agent for the treatment of dry skin according to claim 2, in which the 2-methylspiro (1,3-oxathiolane-5,3')quinuclidine hydrochloride is a cis-isomer.

* * * * *